US009494530B2

(12) United States Patent
Shirata

(10) Patent No.: US 9,494,530 B2
(45) Date of Patent: *Nov. 15, 2016

(54) OPTICAL SENSOR FOR DETECTING LUBRICANT DETERIORATION

(71) Applicant: NABTESCO CORPORATION, Tokyo (JP)

(72) Inventor: Takuya Shirata, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/952,355

(22) Filed: Nov. 25, 2015

(65) Prior Publication Data
US 2016/0084774 A1 Mar. 24, 2016

Related U.S. Application Data

(63) Continuation of application No. 13/991,133, filed as application No. PCT/JP2011/077977 on Dec. 2, 2011, now Pat. No. 9,201,054.

(30) Foreign Application Priority Data

Dec. 2, 2010 (JP) .................. 2010-269097

(51) Int. Cl.
G01N 33/28 (2006.01)
G01N 21/94 (2006.01)
G01N 21/85 (2006.01)
G01N 21/27 (2006.01)
G01N 21/25 (2006.01)

(52) U.S. Cl.
CPC ............. G01N 21/94 (2013.01); G01N 21/27 (2013.01); G01N 21/8507 (2013.01); G01N 33/2888 (2013.01); G01N 21/251 (2013.01); G01N 2201/02 (2013.01); G01N 2201/062 (2013.01)

(58) Field of Classification Search
CPC ..................................... G01N 33/28
USPC ............................................ 356/70
See application file for complete search history.

(56) References Cited

U.S. PATENT DOCUMENTS 2,580,500 A * 1/1952 Mch ................... G01N 21/8507
250/574
3,692,410 A * 9/1972 Jurany ............... G01N 21/8507
356/40

(Continued)

FOREIGN PATENT DOCUMENTS

JP S53-124988 U 10/1978
JP 60-224043 A 11/1985

(Continued)

OTHER PUBLICATIONS

The Final Office Action issued by the U.S Patent Office on Apr. 24, 2014, which is related to U.S. Appl. No. 13/991,132.
An Office Action; "Final Rejection," issued by the Japanese Patent Office on Jul. 1, 2015, which corresponds to Japanese Patent Application No. 2010-269097 and is related to U.S. Appl. No. 13/991,132; with English language translation.

(Continued)

Primary Examiner — Roy M Punnoose

(74) Attorney, Agent, or Firm — Studebaker & Brackett PC

(57) ABSTRACT

A lubricant deterioration sensor mounted in a machine to detect deterioration of a lubricant of the machine, the sensor comprising a white LED for emanating white light, an RGB sensor that detects colors of received light, a clearance forming member in which an oil clearance for intrusion of the lubricant is formed, and a support member that supports the white LED, the RGB sensor, and the clearance forming member; and wherein the clearance forming member allows passage of the light emitted from the white LED, and the oil clearance is placed along an optical path from the white LED to the RGB sensor.

12 Claims, 11 Drawing Sheets

(56) References Cited

U.S. PATENT DOCUMENTS

| | | | | |
|---|---|---|---|---|
| 4,040,743 | A | * | 8/1977 | Villaume .............. G01N 21/532 162/263 |
| 4,114,038 | A | * | 9/1978 | Parker ................... G01N 21/15 250/239 |
| 4,171,909 | A | * | 10/1979 | Kramer ................ G01N 21/255 356/435 |
| 4,534,651 | A | * | 8/1985 | Minikane ............. G01N 21/255 250/227.11 |
| 4,699,509 | A | | 10/1987 | Kamiya et al. |
| 4,851,665 | A | * | 7/1989 | Pesavento ............... E21B 43/17 250/227.23 |
| 5,001,938 | A | * | 3/1991 | Downie ............... G01N 1/2035 250/431 |
| 5,007,740 | A | * | 4/1991 | Jeannotte ........... G01N 21/8507 250/576 |
| 5,069,524 | A | | 12/1991 | Watanabe et al. |
| 5,121,110 | A | | 6/1992 | Mahar, Jr. et al. |
| 5,181,082 | A | * | 1/1993 | Jeannotte ............... G01N 21/83 250/576 |
| 5,194,910 | A | * | 3/1993 | Kirkpatrick, Jr. .. G01N 33/2888 250/573 |
| 5,208,465 | A | | 5/1993 | Jacobson |
| 5,293,107 | A | | 3/1994 | Akeel |
| 5,371,600 | A | * | 12/1994 | Hsia ..................... G01N 15/042 356/436 |
| 5,402,241 | A | * | 3/1995 | Jeannotte ............... G01N 21/83 250/576 |
| 5,404,217 | A | * | 4/1995 | Janik .................. G01N 15/1404 250/576 |
| 5,530,553 | A | * | 6/1996 | Hsia ..................... G01N 15/042 356/436 |
| 5,567,306 | A | | 10/1996 | DeWachter |
| 5,729,006 | A | * | 3/1998 | Maeda ...................... G01D 5/34 250/227.28 |
| 6,546,814 | B1 | | 4/2003 | Choe et al. |
| 7,027,160 | B2 | * | 4/2006 | Sperling .............. G01B 5/0004 356/446 |
| 7,339,657 | B2 | | 3/2008 | Coates |
| 7,612,874 | B2 | * | 11/2009 | Kong .................... G01N 21/314 356/70 |
| 7,916,299 | B2 | * | 3/2011 | Trump .................... G01F 1/704 356/436 |
| 8,155,891 | B2 | * | 4/2012 | Kong .................. G01N 21/8507 356/70 |
| 8,379,192 | B2 | * | 2/2013 | Mannhardt ............ G01N 21/15 356/73 |
| 8,493,561 | B2 | * | 7/2013 | Park ....................... G01N 21/31 356/326 |
| 8,542,363 | B2 | * | 9/2013 | Wynn .................... G01N 21/01 356/246 |
| 8,648,321 | B2 | * | 2/2014 | Schenkel ............ A47L 15/4297 250/227.11 |
| 2002/0005954 | A1 | * | 1/2002 | Sperling .............. G01B 5/0004 356/446 |
| 2003/0142316 | A1 | * | 7/2003 | Schenkl ............... A47L 15/4297 356/442 |
| 2004/0233431 | A1 | | 11/2004 | Ganz et al. |
| 2005/0066707 | A1 | | 3/2005 | Katsuki et al. |
| 2008/0024761 | A1 | * | 1/2008 | Kong .................... G01N 21/314 356/70 |
| 2009/0036250 | A1 | | 2/2009 | Koyama et al. |
| 2009/0086212 | A1 | | 4/2009 | Kitamura |
| 2009/0140754 | A1 | * | 6/2009 | Schenkl ............... A47L 15/4297 324/693 |
| 2009/0216464 | A1 | * | 8/2009 | Kong .................. G01N 21/8507 702/25 |
| 2009/0279072 | A1 | * | 11/2009 | Arakawa ............. G01N 21/314 356/70 |
| 2010/0027015 | A1 | * | 2/2010 | Schweng ............... G01N 21/15 356/437 |
| 2010/0157304 | A1 | * | 6/2010 | Takahashi ............... F16C 19/52 356/442 |
| 2012/0038925 | A1 | * | 2/2012 | Gahr ....................... G01N 21/15 356/440 |
| 2012/0162650 | A1 | * | 6/2012 | Wynn ................. G01N 21/8507 356/432 |
| 2012/0162652 | A1 | * | 6/2012 | Schenkl ............... G01N 21/534 356/436 |
| 2013/0250281 | A1 | | 9/2013 | Shirata |
| 2013/0250303 | A1 | * | 9/2013 | Shirata ..................... B25J 9/102 356/436 |
| 2014/0146307 | A1 | * | 5/2014 | Arrondo ................ G01N 21/25 356/70 |

FOREIGN PATENT DOCUMENTS

| | | |
|---|---|---|
| JP | S60-224042 A | 11/1985 |
| JP | 63-184040 A | 7/1988 |
| JP | H01-501247 A | 4/1989 |
| JP | 01-119741 A | 5/1989 |
| JP | 06-182649 A | 7/1994 |
| JP | 07-118778 A | 5/1995 |
| JP | 07-146233 A | 6/1995 |
| JP | 08-086751 A | 4/1996 |
| JP | 08-126369 A | 5/1996 |
| JP | 10-104160 A | 4/1998 |
| JP | H10-268159 A | 10/1998 |
| JP | H11-271217 A | 10/1999 |
| JP | 2000-146696 A | 5/2000 |
| JP | 2001-242079 A | 9/2001 |
| JP | 2002-006039 A | 1/2002 |
| JP | 20020162407 A1 | 11/2002 |
| JP | 2004-191607 A | 7/2004 |
| JP | 20070046936 A1 | 3/2007 |
| JP | 2007-198767 A | 8/2007 |
| JP | 2007-278903 A | 10/2007 |
| JP | 20090228239 A1 | 9/2009 |
| JP | 2009-226488 A | 10/2009 |
| JP | 4523977 B2 | 8/2010 |
| JP | 2012-143837 A | 8/2012 |
| WO | 88/02109 A1 | 3/1988 |
| WO | 99/49302 A | 9/1999 |
| WO | 2007/091568 A | 8/2007 |

OTHER PUBLICATIONS

An Office Action; "Final Rejection," issued by the Japanese Patent Office on Jun. 17, 2015, which corresponds to Japanese Patent Application No. 2011-003853 and is related to U.S. Appl. No. 13/991,132; with English language translation.

International Search Report; PCT/JP2011/077977; Mar. 6, 2012.

The non-final Office Action issued by the U.S. Patent Office on May 22, 2015, which corresponds to U.S. Appl. No. 13/991,132 and is related to U.S. Appl. No. 13/991,133.

International Search Report; PCT/JP2011/077980; Mar. 6, 2012.

Non-Final Office Action issued by the U.S Patent Office on Aug. 15, 2014, which is related to U.S. Appl. No. 13/991,132.

An Office Action; "Notification of Reasons for Refusal," issued by the Japanese Patent Office on Nov. 6, 2014, which corresponds to Japanese Patent Application No. 2010-269097 and is related to U.S. Appl. No. 13/991,133; with English language translation.

An Office Action; "Notification of Reasons for Refusal," issued by the Japanese Patent Office on Nov. 18, 2014, which corresponds to Japanese Patent Application No. 2011-003853 and is related to U.S. Appl. No. 13/991,133; with English language translation.

The final Office Action issued by the U.S. Patent Office on Jan. 18, 2015, which corresponds to U.S. Appl. No. 13/991,132 and is related to U.S. Appl. No. 13/991,133.

An Office Action; "Notification of Reasons for Refusal" issued by the Japanese Patent Office on Aug. 2, 2016, which corresponds to Japanese Patent Application No. 2015-195098 and is related to U.S. Appl. No. 14/952,355; with English language translation.

* cited by examiner

OPTICAL SENSOR FOR DETECTING LUBRICANT DETERIORATION

TECHNICAL FIELD

The invention relates to an optical sensor for detecting deterioration of a machine lubricant.

BACKGROUND ART

As a lubricant deterioration sensor, an oil deterioration sensor in which an oil intrusion clearance for intrusion of a lubricant is formed on an optical path from an infrared LED (Light Emitting Diode) to a photodiode has been known. The oil deterioration sensor detects an amount of light which exits from the infrared LED and is absorbed by the lubricant in the oil intrusion clearance based on an amount of light received by the photodiode, and determines a degree of deterioration of the lubricant that correlates to the detected amount of absorbed light (see; for instance, Patent Documents 1 and 2).

However, the oil deterioration sensor described in Patent Documents 1 and 2 can detect a concentration of insoluble substance in the lubricant as a degree of deterioration of the lubricant but has a problem that types of contaminants in the lubricant can not be specified.

As a technique for specifying a type of contaminant in a lubricant, a technique in which a light is irradiated to a membrane filter by an LED after filtration of a lubricant is known. In the technique, a light reflected from contaminants on the membrane filer is converted by a light receiving element into RGB digital values, and types of the contaminants in the lubricant are specified according to the converted RGB digital values (see; for instance, Non-Patent Documents 1 and 2).

CITATION LIST

Patent Documents

Patent Document 1: JP-A-7-146233
Patent Document 2: JP-A-10-104160
Non-Patent Document 1: Tomohiko YAMAGUCHI, four others, "Method for determining hues of contaminants in a lubricant," Engineering Department of Fukui University, Study Report March 2003, Vol. 51, No. 1, pp. 81 to 88.
Non-Patent Document 2: Tomonori HONDA, "Technique for diagnosing and inspecting deterioration of a lubricant," Academic Journal of Precision Engineering, 2009, Vo. 75, No. 3, pp. 359-362

SUMMARY OF INVENTION

Technical Problem

However, in the techniques described in Non-Patent Documents 1 and 2, it is needed to sample a lubricant from a machine and to filter the sample by a membrane filter. Accordingly, the techniques have a problem that an instancy is inferior.

Accordingly, an object of the present invention is to provide a lubricant deterioration sensor capable of instantly specifying types of contaminants in a lubricant of a machine.

Solution to Problem

An optical sensor, comprising:
a light emitting element for emanating light;
a light receiving element for detecting the light, disposed adjacent to the light emitting element;
a clearance forming member forming a fluid clearance in which a fluid enters;
a support member supporting the light emitting element, the light receiving element and the clearance forming member;
an optical path surrounding member, wherein
the clearance forming member is transmissive so that the light emitted from the light emitting element,
the fluid clearance is provided on an optical path from the light emitting element to the light receiving element, and
the optical path surrounding member surrounds at least a portion of the optical path.

By means of the configuration, the optical sensor of the invention detects colors from light of, among white light rays emitted from the white light emitting element, wavelengths that are not absorbed by contaminants in the fluid at the fluid clearance by use of the color light receiving element, so that colors of the contaminants in the fluid of the machine can be instantly detected. In other words, the optical sensor of the invention can instantly specify, on the basis of the colors detected by the color light receiving element, types of contaminants in the fluid of the machine. Further, the optical path surrounding member covers the optical path so as to suppress effects by disturbance, thus the detection accuracy can be improved.

In the lubricant deterioration sensor according to the present invention,
a space provided on the optical path between the light emitting element and the clearance forming member may be formed by a hole, and
a space provided on the optical path between the light receiving element and the clearance forming member may be formed by a hole.

By means of the configuration, the optical path can be prevented from occurring a diffused reflection, thus the detection accuracy can be improved.

In the lubricant deterioration sensor according to the present invention,
the light emitting element and the light receiving element may be accommodated in the optical path surrounding member at a position opposite to the clearance forming member. By means of the configuration, the light emitting element and the light receiving element can be protected from being affected from the thermal of the fluid, thus the detection accuracy can be improved.

In the lubricant deterioration sensor according to the present invention, the clearance forming member may have two rectangular prisms each of which has the reflection surface for bending the optical path, so that the optical path is bent by the reflection surfaces of the two rectangular prisms, and the oil clearance may be formed between the two rectangular prisms.

The configuration makes it possible to miniaturize the lubricant deterioration sensor of the invention by means of a simple configuration including a smaller number of parts.

The lubricant deterioration sensor according to the present invention may further include a screw portion configured to fix the optical sensor to a mating member, wherein the optical path surrounding member is disposed inside of the screw portion.

By means of the configuration, the configuration makes it possible to miniaturize the lubricant deterioration sensor of the invention by means of a simple configuration including a smaller number of parts In the lubricant deterioration sensor according to the present invention, a width of a space on the optical path between the light emitting element and the clearance forming member at a side of the clearance forming member may be shorter than a width of the space at a side of the light emitting element, and the optical path between the light emitting element and the clearance forming member and the optical path between the light receiving element and the clearance forming member may extend in a direction in which the optical sensor is inserted to a mating member.

By means of the configuration, the activity for assembling can be improved.

In the lubricant deterioration sensor according to the present invention, a groove surrounding an opening of a space on the optical path between the light emitting element and the clearance forming member may be formed on a surface of the supporting member to which the clearance forming member is attached. By means of the configuration, the adhesive for attaching the clearance forming member can be prevented from irrupting into the space on the optical path.

An optical sensor, comprising:

a light emitting element that emits a light;

a light receiving element that detects the light;

a transmissive part that includes an incident surface to which the light is incident from the light emitting element and an exit surface from which the light incident on the incident surface, and defines a gap, into which a lubricant enters, in an optical path from the incident surface to the exit surface; and a first narrowing part that narrows the optical path from the light emitting element to the incident surface.

The first narrowing part may include a first part defining a first hole in which the light emitting element is accommodated; and a second part defining a second hole which communicates the first hole with the incident surface and has a first narrowed portion, and an area of the optical path in the first narrowed portion may be smaller than an area of the optical path in the first hole.

The optical sensor may further comprise a second narrowing part that narrows the optical path from the exit surface to the light receiving element.

The second narrowing part may include a third part defining a third hole in which the light receiving element is accommodated; and a fourth part defining a fourth hole which communicates the third hole with the exit surface and has a second narrowed portion. An area of the optical path in the second narrowed portion may be smaller than an area of the optical path in the third hole.

The optical sensor may be configured such that:

the transmissive part includes a first rectangular prism and a second rectangular prism, the first rectangular prism has:

a first incident surface which is the incident suface;

a first exit surface orthogonal to the first incident surface;

a first reflection surface which is an inclined surface with respect to an apex angle being right angle and which bends the optical path of the light incident on the first incident surface;

a pair of first side surfaces which sandwitch the first incident surface, the first exit surface and the first reflection surface, the second rectangular prism has:

a second incident surface which opposes the first exit surface;

a second exit surface which is orthogonal to the second incident surface and which is the exit surface;

a second reflection surface which is an inclined surface with respect to an apex angle being right angle and which bends the optical path of the light incident on the second incident surface;

a pair of first side surfaces which sandwitch the first incident surface, the first exit surface and the first reflection surface, at least one of the first rectangular prism and the second rectangular prism is an object to be fixed, the optical sensor includes a wall to which a surface including the side surfaces is fixed, in the object to be fixed.

The optical sensor may further comprise a supporting member which supports the light emitting element, the light receiving element and the transmissive part. The supporting member may include the first narrowing part.

DESCRIPTION OF EMBODIMENTS

An embodiment of the invention is hereunder described by reference to the drawings.

First, a configuration of a lubricant deterioration sensor of the embodiment is described.

Figure 1:
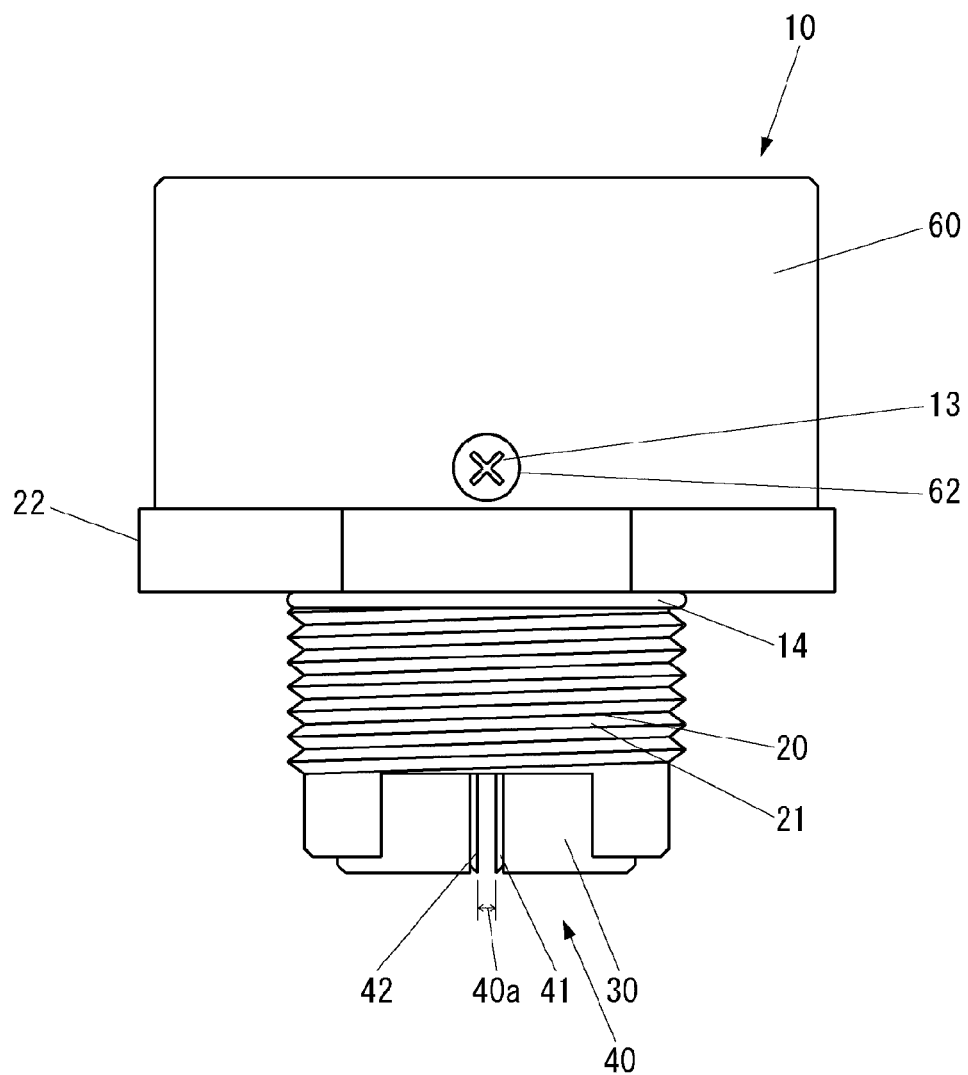
FIG. 1 is a front view of a lubricant deterioration sensor of one embodiment of the invention.
Figure 2:
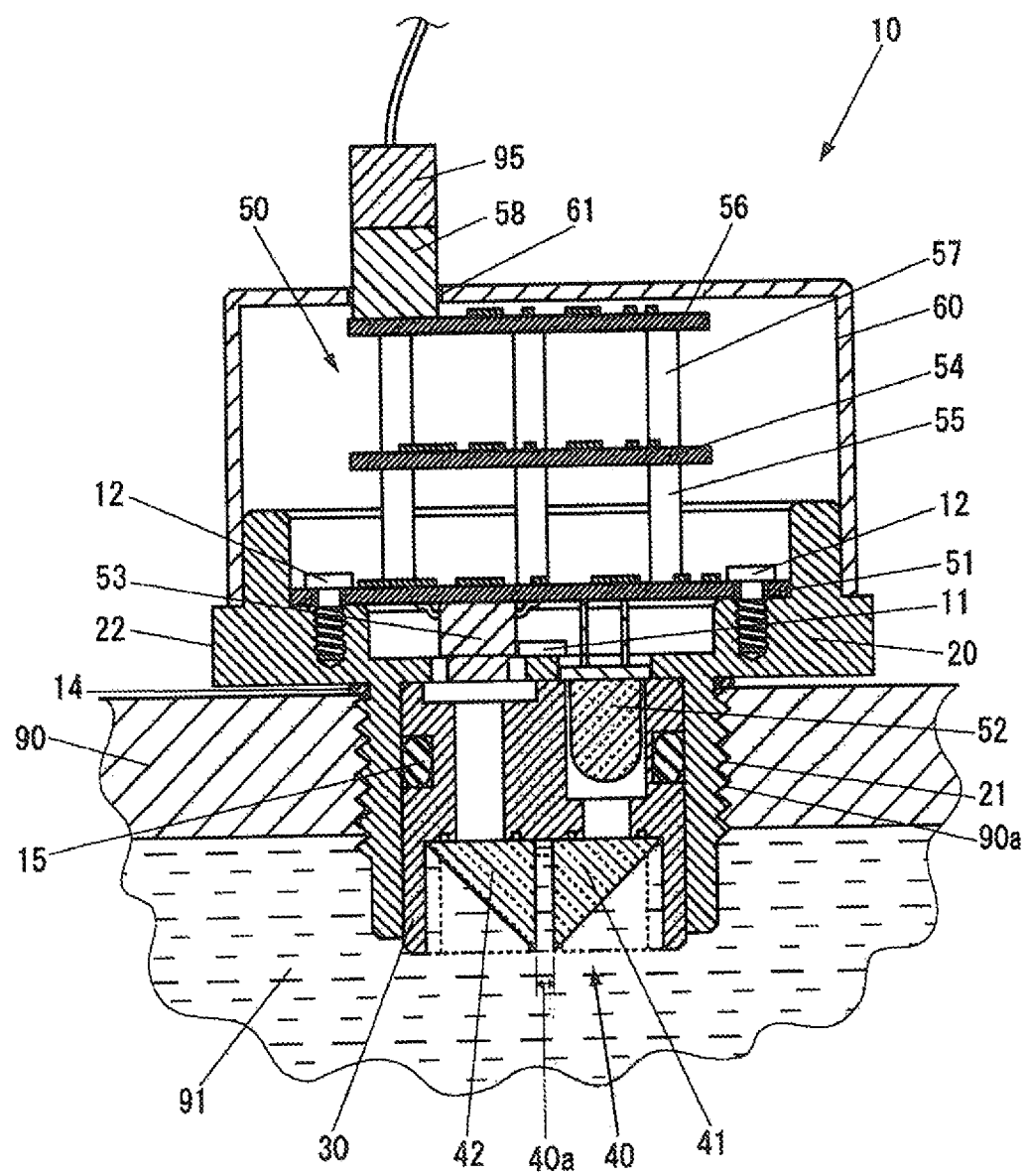
FIG. 2 is a front cross sectional view of the lubricant deterioration sensor shown in FIG. 1.

FIG. 1 is a front view of an optical sensor 10 of the embodiment. FIG. 2 is a front cross sectional view of the lubricant deterioration sensor 10 mounted in a machine 90. In this embodiment, the optical sensor is used as a lubricant deterioration sensor 10.

As shown in FIGS. 1 and 2, the lubricant deterioration sensor 10 is an apparatus for detecting deterioration of a lubricant 91 of the machine 90 mounted in the machine 90. Although in the present embodiment this sensor 10 is used for the oil or the lubricant as an example, the sensor 10 can be used for any other fluid.

The lubricant deterioration sensor 10 includes a support member 20 that is made of an aluminum alloy for supporting respective parts of the lubricant deterioration sensor 10, a holder 30 that is secured to the support member 20 with a screw 11 and that is made of an aluminum alloy; a clearance forming member 40 that is retained by the holder 30, an electronic parts group 50 outfitted with a circuit board 51 that is secured to the support member 20 with screws 12, and a cover 60 that is secured to the support member 20 with a screw 13 and that is made of an aluminum alloy.

The clearance forming member 40 is made up of two rectangular glass prisms 41 and 42, and an oil clearance 40a that is a clearance for intrusion of the lubricant 91 is formed between the two rectangular prisms 41 and 42.

The electronic parts group 50 includes a white LED 52 mounted on the circuit board 51, an RGB sensor 53 mounted on the circuit board 51, a circuit board 54 placed opposite the white LED 52 and the RGB sensor 53 with reference to the circuit board 51, a plurality of columns 55 for anchoring the circuit board 51 and the circuit board 54, a circuit board 56 placed opposite the circuit board 51 with reference to the circuit board 54, a plurality of columns 57 for securing the circuit board 54 and the circuit board 56; and a connector 58 mounted opposite the circuit board 54 with reference to the circuit board 56. A plurality of electronic parts are mounted on the circuit board 51, the circuit board 54, and the circuit board 56. Further, the circuit board 51, the circuit board 54, and the circuit board 56 are electrically connected to each other.

The lubricant deterioration sensor 10 is equipped with an O ring 14 for preventing leakage of the lubricant 91 from a clearance between the support member 20 and the machine 90 and an O ring 15 for preventing leakage of the lubricant 91 from a clearance between the support member 20 and the holder 30.

Figure 3A:
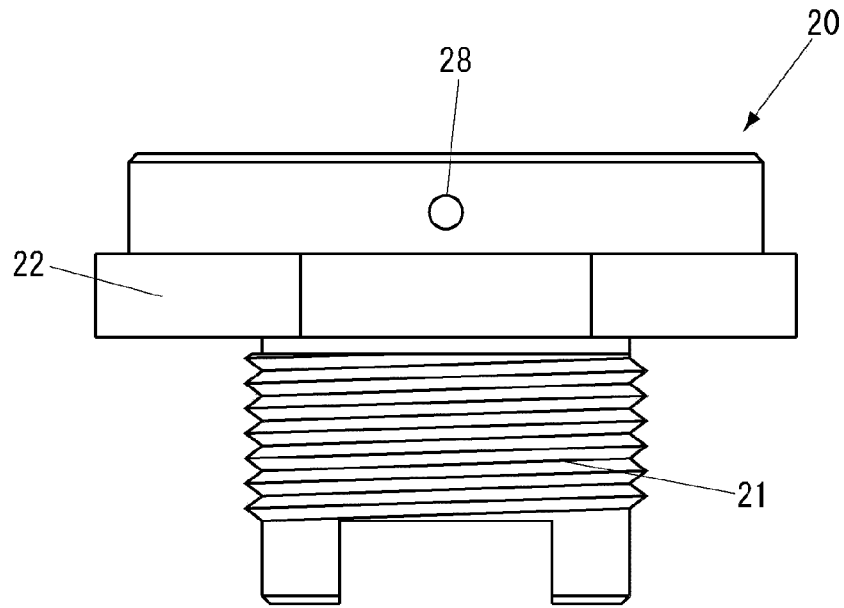
FIG. 3A it is a front view of a support member shown in FIG. 1.
Figure 3B:
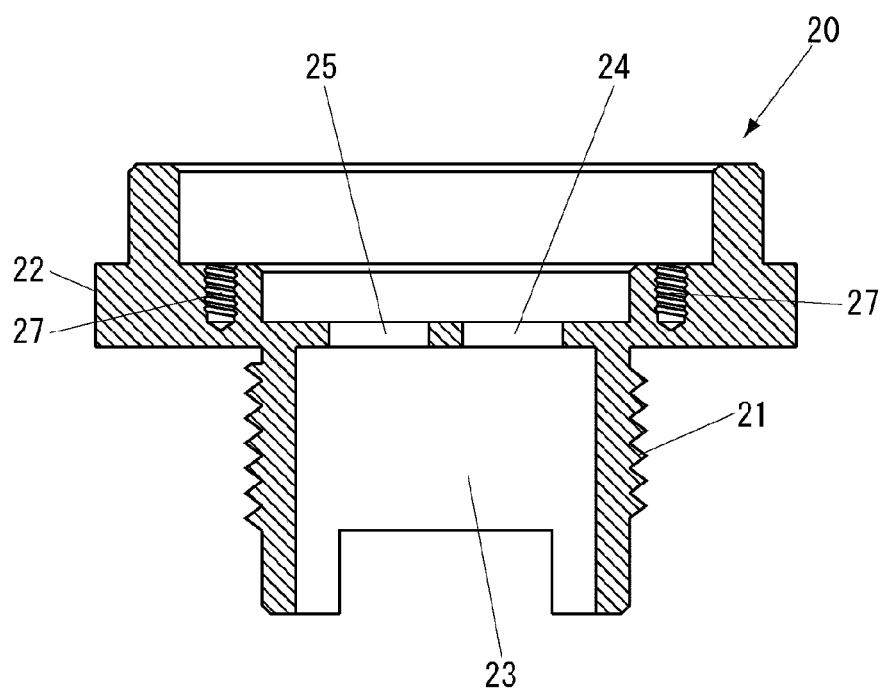
FIG. 3B is a front cross sectional view of the support member shown in FIG. 1.
Figure 4A:
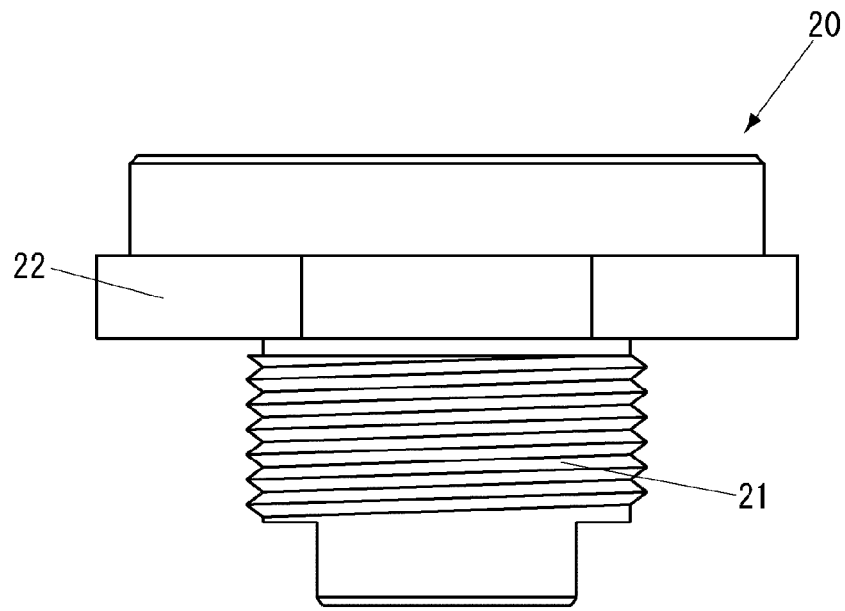
FIG. 4A it is a side view of the support member shown in FIG. 1.
Figure 4B:
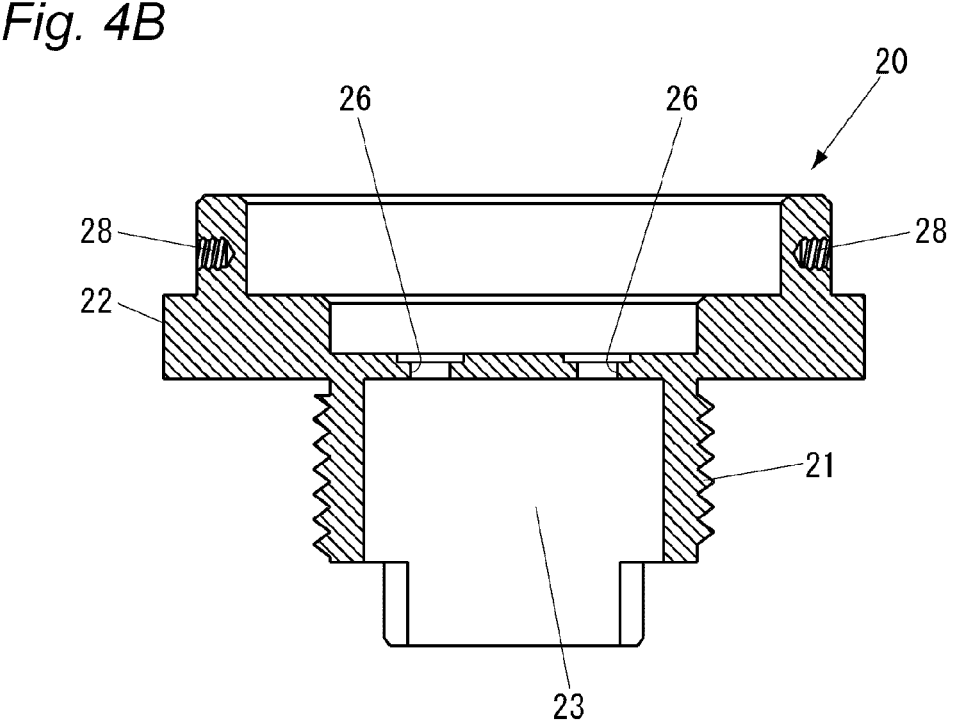
FIG. 4B is a side cross sectional view of the support member shown in FIG. 1.
Figure 5A:
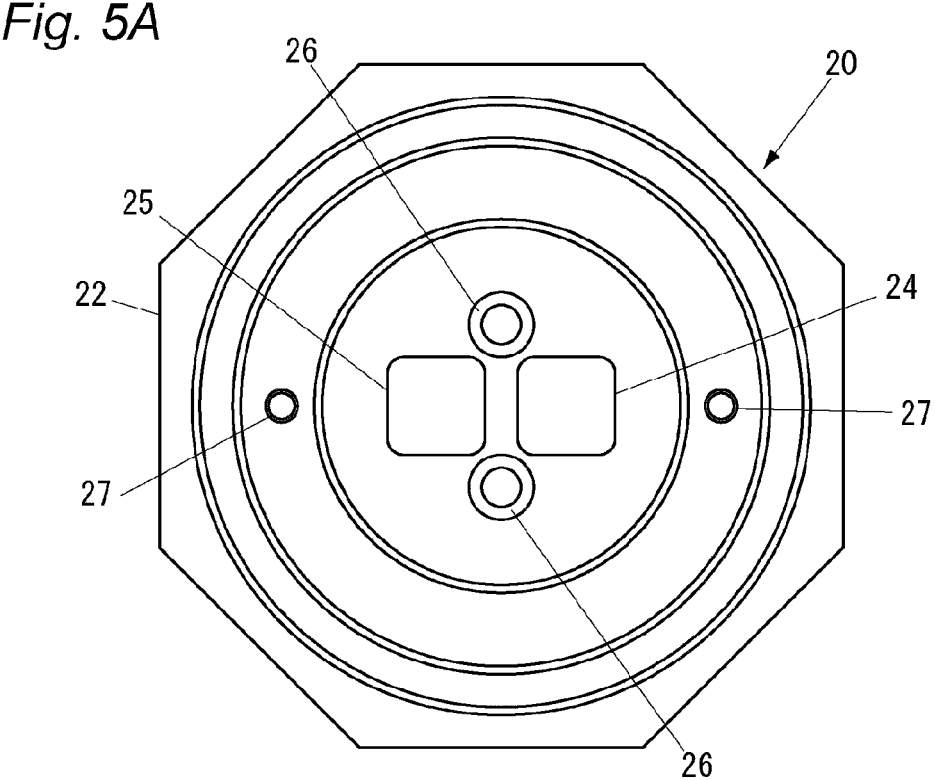
FIG. 5A is a plan view of the support member shown in FIG. 1.
Figure 5B:
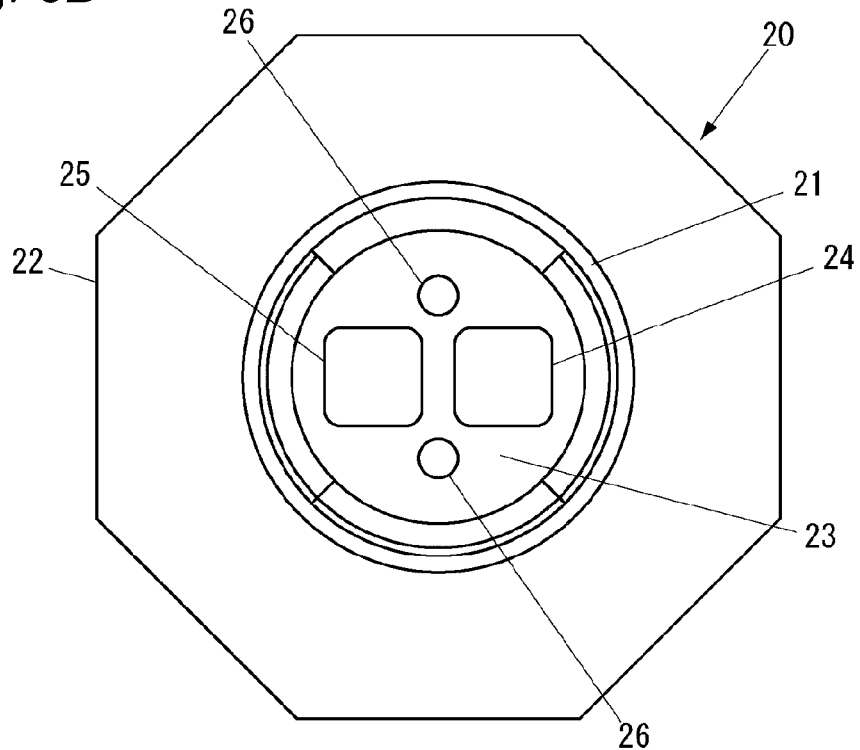
FIG. 5B is a bottom view of the support member shown in FIG. 1.

FIG. 3A is a front view of the support member 20. FIG. 3B is a front cross sectional view of the support member 20. FIG. 4A is a side view of the support member 20. FIG. 4B is a side cross sectional view of the support member 20. FIG. 5A is a plan view of the support member 20. FIG. 5B is a bottom view of the support member 20.

As shown in FIGS. 1 to 5B, the support member 20 includes a screw section 21 secured to a tapped hole 90a of the machine 90, a hexagonal tool contact 22 that is to be gripped with a tool when the screw section 21 is rotated with respect to the tapped hole 90a of the machine 90, and a holder housing section 23 for housing the holder 30. Moreover, the support member 20 are formed with a hole 24 for insertion of the white LED 52, a hole 25 for insertion of the RGB sensor 53, two holes 26 for insertion of the screw 11, two tapped holes 27 for insertion of the screws 12, and two tapped holes 28 for insertion of the screw 13.

The support member 20 supports the white LED 52 and the RGB sensor 53 by way of the circuit board 51. The support member 20 supports the clearance forming member 40 by way of the holder 30.

Figure 6A:
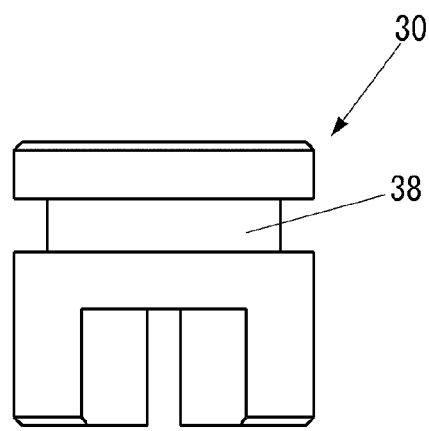
FIG. 6A is a front view of a holder shown in FIG. 1.
Figure 6B:
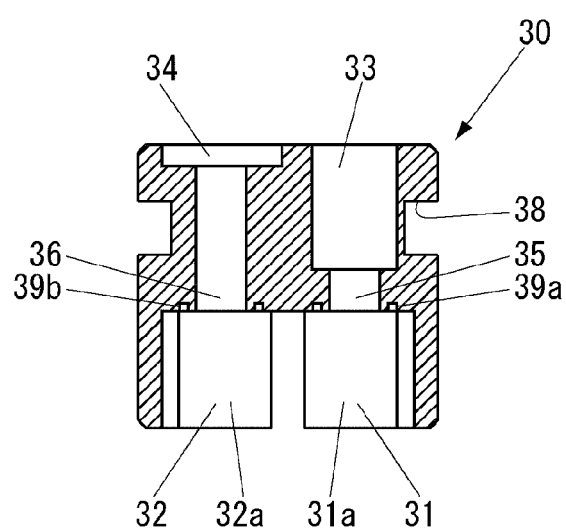
FIG. 6B is a front cross sectional view of the holder shown in FIG. 1.
Figure 7A:
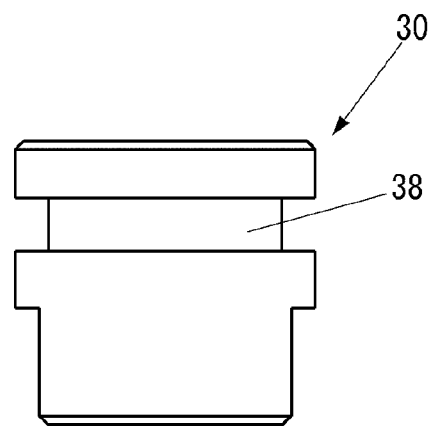
FIG. 7A is a side view of the holder shown in FIG. 1.
Figure 7B:
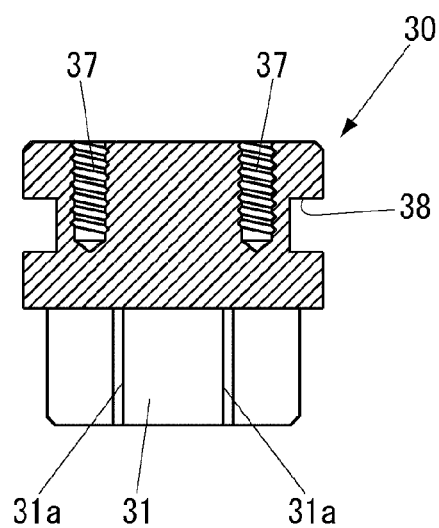
FIG. 7B is a side cross sectional view of the holder shown in FIG. 1.
Figure 8A:
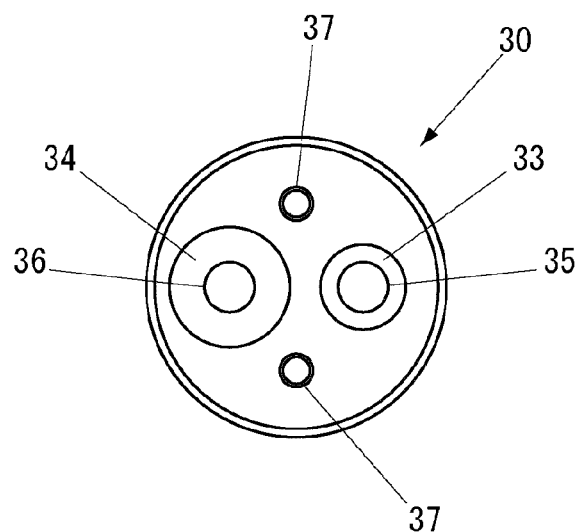
FIG. 8A is a plan view of the holder shown in FIG. 1.
Figure 8B:
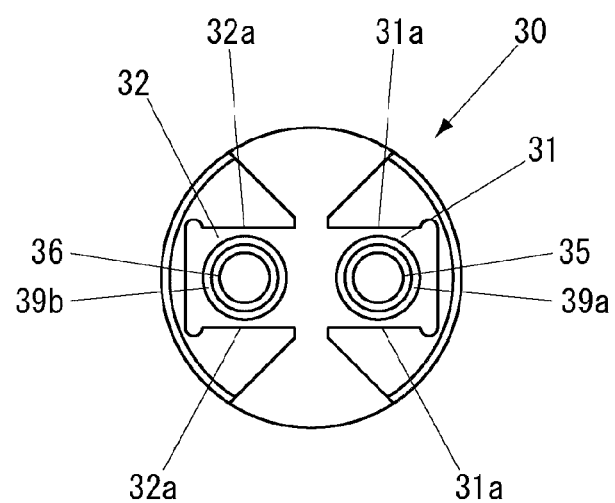
FIG. 8B is a bottom view of the holder shown in FIG. 1.
Figure 9:
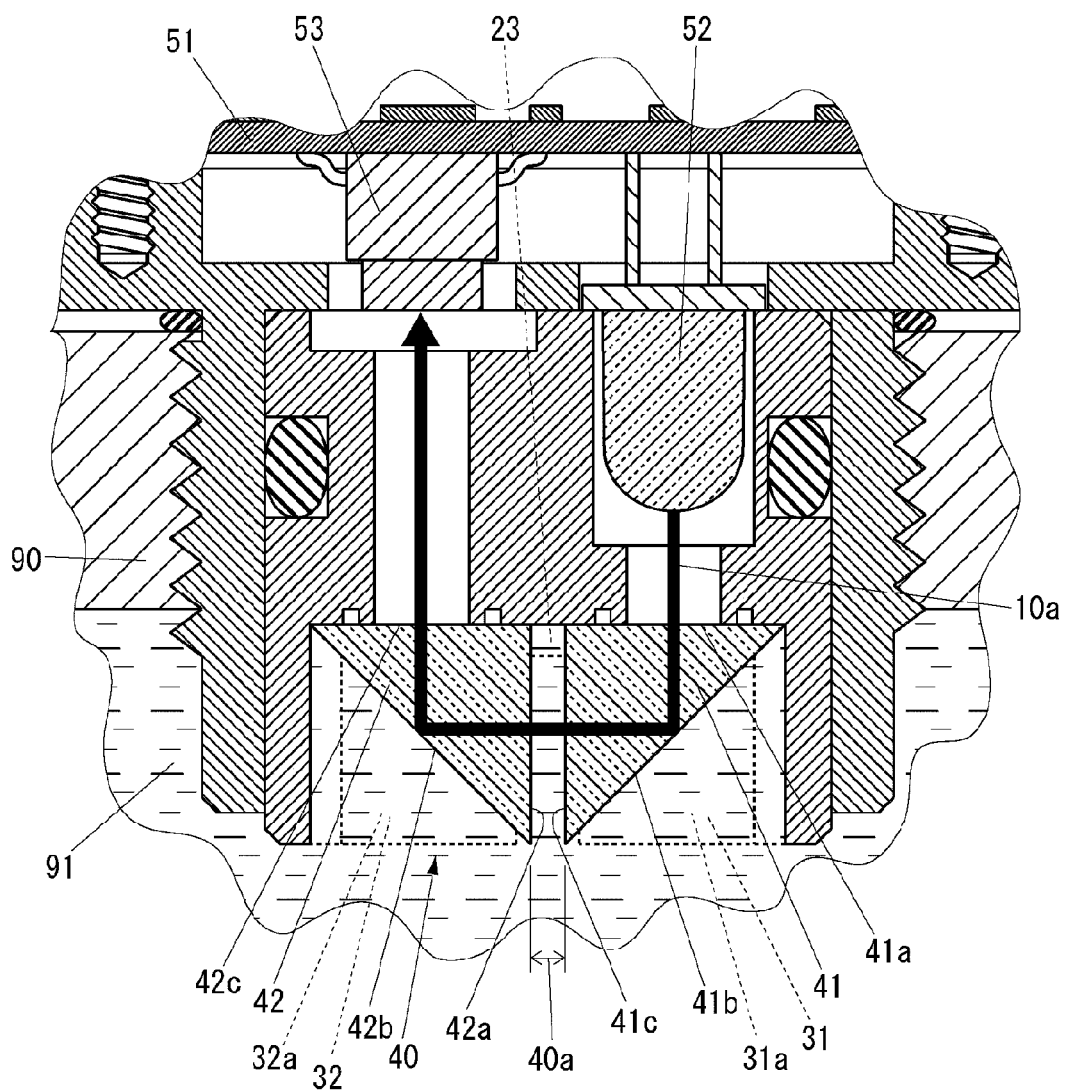
FIG. 9 is a view showing an optical path from a white LED to an RGB sensor shown in FIG. 2.

FIG. 6A is a front view of the holder 30. FIG. 6B is a front cross sectional view of the holder 30. FIG. 7A is a side view of the holder 30. FIG. 7B is a side cross sectional view of the holder 30. FIG. 8A is a plan view of the holder 30. FIG. 8B is a bottom view of the holder 30. FIG. 9 is a view showing an optical path 10a from the white LED 52 to the RGB sensor 53.

As shown in FIGS. 1 and 2 and FIGS. 6A to 9, the holder 30 includes a prism housing 31 that houses the rectangular prism 41, a prism housing 32 that houses the rectangular prism 42, and an LED housing 33 that houses the white LED 52. The holder 30 are formed with a hole 34 for the RGB sensor 53, a hole 35 that establishes mutual communication between the prism housing 31 and the LED housing 33, a hole 36 that establishes mutual communication between the prism housing 32 and the hole 34, two tapped holes 37 for screw-engagement of the screw 11, a groove 38 to which the O ring 15 fits, an annular groove 39a for preventing an adhesive which fixes the rectangular prism 41 to the prism housing 31 from entering the hole 35, and an annular groove 39b for preventing an adhesive which fixes the rectangular prism 42 to the prism housing 32 from entering the hole 36. The grooves 39a, 39b for preventing the adhesive from entering the holes 35, 36 may be provided on the support member 20.

The prism housing 31 includes two walls 31a between which the rectangular prism 41 is to be inserted. The walls 31a fix the rectangular prism 41 by means of an adhesive. The prism housing 32 includes two walls 32a between which the rectangular prism 42 is to be inserted. The walls 32a fix the rectangular prism 42 by means of an adhesive.

The holder 30 surrounds at least a portion of the optical path 10a from the white LED 52 to the RGB sensor 53 by means of the LED housing 33, the hole 35, the prism housing 31, the prism housing 32, the hole 36, the hole 34, making up an optical path surrounding member of the invention. The grooves 39a, 39b for preventing the adhesive from entering the holes 35, 36 may be provided on the optical path surrounding member.

A surface of the holder 30 is treated by antireflection; for instance, mat black anodized aluminum treatment.

As shown in FIG. 9, the oil clearance 40a of the clearance forming member 40 is placed on the optical path 10a from the white LED 52 to the RGB sensor 53.

The rectangular prisms 41 and 42 are transmissive so that light emitted from the white LED 52 transmits therethrough. The rectangular prism 41 has an incident surface 41a on which light emitted by the white LED 52 falls, a reflection surface 41b that reflects the light fell on the incident surface 41a, to thus make a 90-degree turn of a traveling direction of light, and an exit surface 41c from which the light reflected by the reflection surface 41b exits. The rectangular prism 42 has an incident surface 42a on which light exited from the exit surface 41c of the rectangular prism 41 falls, a reflection surface 42b that reflects the light fell on the incident surface 42a, to thus make a 90-degree turn of a traveling direction of light, and an exit surface 42c from which the light reflected by the reflection surface 42b exits.

The incident surface 41a, the reflection surface 41b, and the exit surface 41c of the rectangular prism 41, and the incident surface 42a, the reflection surface 42b, and the exit surface 42c of the rectangular prism 42 are optically polished. The reflection surface 41b of the rectangular prism 41 and the reflection surface 42b of the rectangular prism 42 each are covered with an aluminum evaporated film. In order to protect the aluminum evaporated film that has a low degree of hardness and adhesion, the aluminum evaporated film is further coated with an $SiO_2$ film.

The optical path 10a is bent at 90-degree angle on the reflection surface 41b of the rectangular prism 41, further is bent at 90-degree angle also on the reflection surface 42b of the rectangular prism 42. To be specific, the optical path 10a is bent at 180 degrees angle by the clearance forming member 40.

A distance between the exit surface 41c of the rectangular prism 41 and the incident surface 42a of the rectangular prism 42 is a length of the oil clearance 40a. The length of the oil clearance 40a is 1 millimeter for instance. When the length of the oil clearance 40a is too short, contaminants in the lubricant 91 become difficult to flow through the oil clearance 40a appropriately, so that a degree of detection accuracy of a color of the contaminants in the lubricant 91 deteriorates. In the meantime, when the length of the oil clearance 40a is too long, light emitted from the white LED 52 is too absorbed by the contaminants in the lubricant 91 in the oil clearance 40a to reach the RGB sensor 53, so that the degree of detection accuracy of the color of the contaminants in the lubricant 91 also deteriorates. Consequently, it is preferable that the length of the oil clearance 40a be appropriately set such that the degree of detection accuracy of the color of the contaminants in the lubricant 91 improves.

The white LED 52 is an electronic part that emits white light and makes up a light emitting element of the invention. For instance, NSPW500GS-K1 manufactured by Nichia Corporation, can be used as the white LED 52. Although in the present embodiment the white LED 52 is used as the light emitting element, the light emitting element can be any other light emitting device. The light emitted by the light emitting element is preferably visible light, but may be light having wavelength other than the visible light.

The RGB sensor 53 is an electronic part that detects a color of received light and makes up a color light receiving element of the invention. For instance, S9032-02 manufactured by Hamamatsu Photonics K.K. can be used as the RGB sensor 53.

As shown in FIG. 2, the connector 58 is connected to a connector 59 of an external device of the lubricant deterioration sensor 139a and is fed with electric power from the external device by way of a connector 95. A detection result of the lubricant deterioration sensor 10 is output to the external device as an electric signal by way of the connector 95.

Figure 10A:
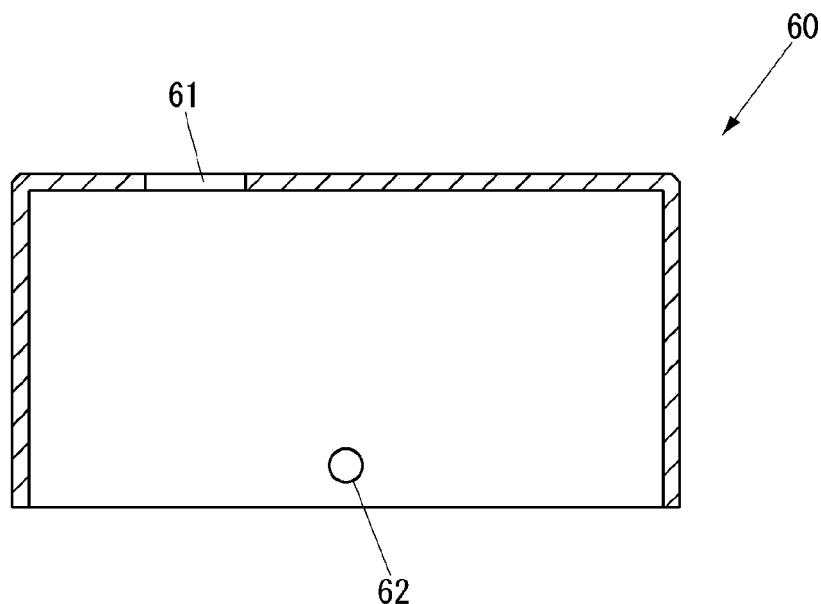
FIG. 10A is a front cross sectional view of a cover shown in FIG. 1.
Figure 10B:
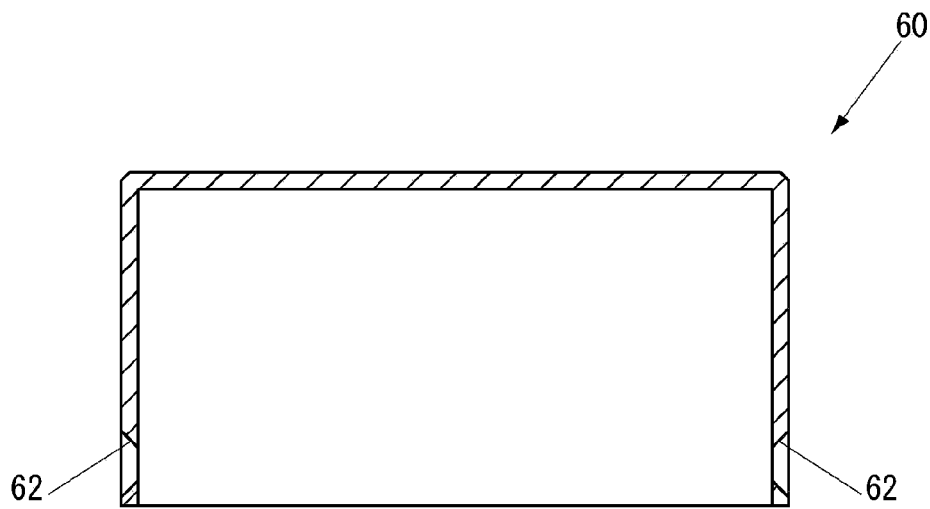
FIG. 10B is a side cross sectional view of the cover shown in FIG. 1.
Figure 11A:
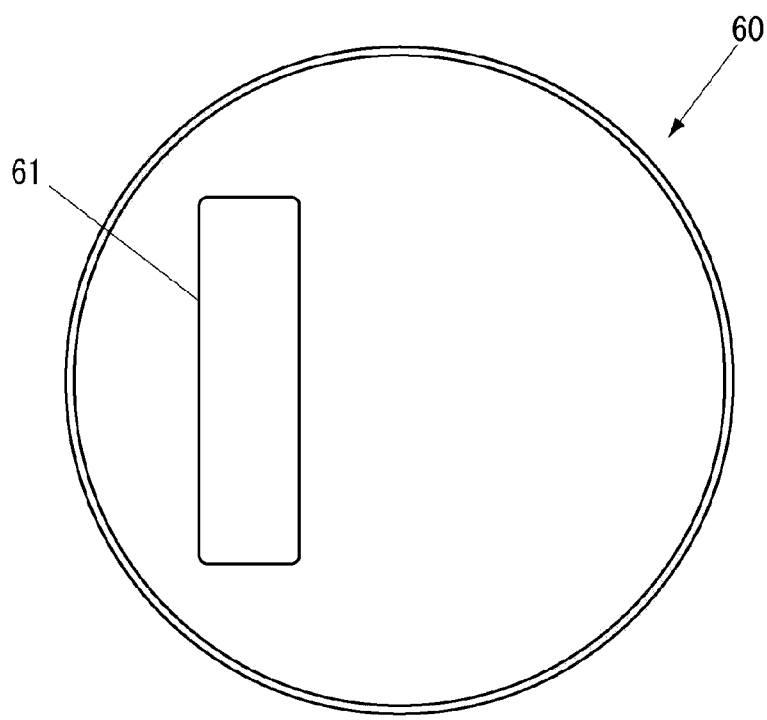
FIG. 11A is a plan view of the cover shown in FIG. 1.
Figure 11B:
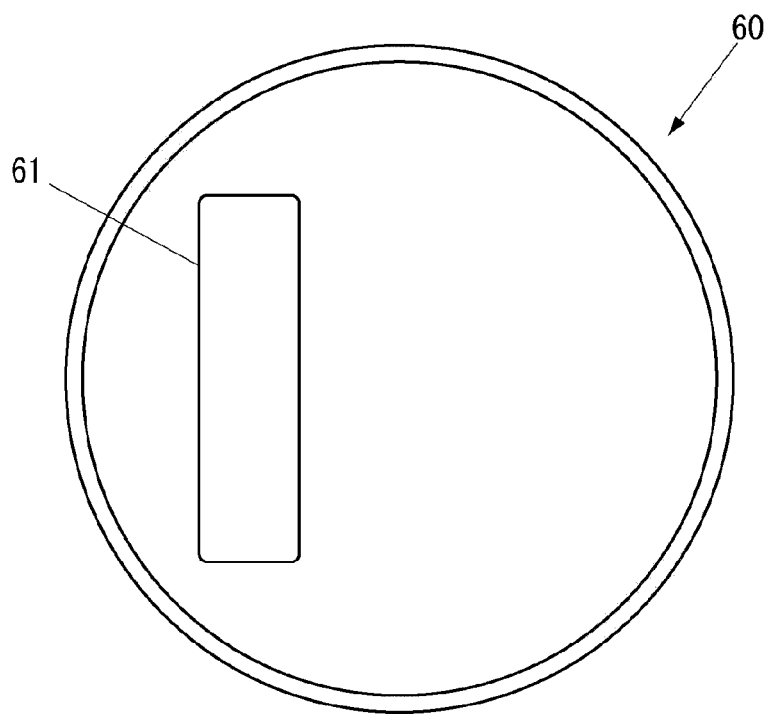
FIG. 11B is a bottom view of the cover shown in FIG. 1.

FIG. 10A is a front cross sectional view of the cover 60. FIG. 10B is a side cross sectional view of the cover 60. FIG. 11A is a plan view of the cover 60. FIG. 11B is a bottom view of the cover 60.

As shown in FIGS. 1, 2, 10A to 11B, the cover 60 has a hole 61 for insertion of the connector 58 and two holes 62 for insertion of the screw 13.

A surface of the cover 60 is treated by antireflection; for instance, mat black anodized aluminum treatment.

The optical sensor 10 includes a first narrowing part that narrows the optical path 10a from the light emitting element 52 to the incident surface 41a.

The first narrowing part includes a first part defining a first hole in which the light emitting element 52 is accommodated, a second part defining a second hole which communicates the first hole with the incident surface 41a and has a first narrowed portion. An area of the optical path 10a in the first narrowed portion is smaller than an area of the optical path 10a in the first hole.

The optical sensor 10 includes a second narrowing part that narrows the optical path 10a from the exit surface 42c to the light receiving element 53.

The second narrowing part includes a third part defining a third hole in which the light receiving element 53 is accommodated, and a fourth part defining a fourth hole which communicates the third hole with the exit surface 42c and has a second narrowed portion. An area of the optical path 10a in the second narrowed portion is smaller than an area of the optical path 10a in the third hole.

The first rectangular prism 41 has a first incident surface which is the incident surface 41a, a first exit surface 41c orthogonal to the first incident surface 41a, a first reflection surface 41b which is an inclined surface with respect to an apex angle being right angle and which bends the optical path 10a of the light incident on the first incident surface 41a, a pair of first side surfaces which sandwich the first incident surface 41a, the first exit surface 41c and the first reflection surface 41b.

The second rectangular prism 42 has a second incident surface 42a which opposes the first exit surface 41c, a second exit surface 42c which is orthogonal to the second incident surface 42a and which is the exit surface 42c, a second reflection surface 42b which is an inclined surface with respect to an apex angle being right angle and which bends the optical path 10a of the light incident on the second incident surface 42a, a pair of second side surfaces which sandwich the second incident surface 42a, the second exit surface 42c and the second reflection surface 42b.

At least one of the first rectangular prism 41 and the second rectangular prism 42 is an object to be fixed. The optical sensor 10 includes a wall to which a surface including the side surfaces is fixed, in the object to be fixed.

The support member 20 which supports the light emitting element 52, the light receiving element 53 and the transmissive part 41, 42. The support member 20 includes the first narrowing part.

Next, a method for assembling the lubricant deterioration sensor 10 is described.

First, an adhesive is applied to two surfaces of the surfaces of the rectangular prism 41 that contact the two walls 31a of the prism housing 31 as well as to an outer peripheral surface of the groove 39a that contacts the incident surface 41a of the rectangular prism 41 of the prism housing 31 of the holder 30, whereby the rectangular prism 41 is secured to the prism housing 31 by means of the adhesive. In addition, an adhesive is applied to two surfaces of the surfaces of the rectangular prism 42 that contact the two walls 32a of the prism housing 32 as well as to an outer peripheral surface of the groove 39b which contacts the exit surface 42c of the rectangular prism 42 of the prism housing 32 of the holder 30, whereby the rectangular prism 42 is secured to the prism housing 32 by means of the adhesive. Further, the white LED 52 is secured to the LED housing 33 of the holder 30 by means of the adhesive.

Next, the holder 30 outfitted with the O ring 15 is secured, by means of the screw 11, to the holder housing 23 of the support member 20 outfitted with the O ring 14.

The electronic parts group 50 into which various electronic parts except the white LED 52; namely, the circuit board 51, the RGB sensor 53, and the connector 58, are previously assembled is secured to the support member 20 by the screws 12, thereby the white LED 52 is soldered to the circuit board 51.

Finally, the cover 60 is secured to the support member 20 by the screw 13.

A method for mounting the lubricant deterioration sensor 10 to the machine 90 is now described.

First, the tool contact 22 of the support member 20 is pinched with a tool, and the screw 21 of the support member 20 is screwed into the tapped hole 90a of the machine 90, whereby the lubricant deterioration sensor 10 is secured to the machine 90.

The connector 95 of an external device of the lubricant deterioration sensor 10 is connected to the connector 58.

Next, operation of the lubricant deterioration sensor 10 is described.

In the lubricant deterioration sensor 10, white light is emitted from the white LED 52 by means of the electric power fed from an external device by way of the connector 58.

The lubricant deterioration sensor 10 outputs amounts of RGB colors of light received by the RGB sensor 53 as an electric signal to an external device by way of the connector 58.

The lubricant deterioration sensor 10 can also be separately equipped with a sensor other than the RGB sensor 53. For instance, when a temperature sensor for detecting a temperature of the lubricant 91 is included in the electronic parts group 50, the lubricant deterioration sensor 10 can output a temperature detected by the temperature sensor to an external device as an electric signal by way of the connector 58.

As described above, the lubricant deterioration sensor 10 detects colors from light of, among white light rays emitted from the white LED 52, wavelengths that are not absorbed by contaminants in the lubricant 91 in the oil clearance 40a by use of the RGB sensor 53, so that colors of the contaminants in the lubricant 91 of the machine 91 can be instantly detected. In other words, the lubricant deterioration sensor can instantly specify, on the basis of the colors detected by the RGB sensor 53, types and amounts of contaminants in the lubricant 91 of the machine 90 by use of an external device, like a computer. Incidentally, the lubricant deterioration sensor 10, electronic parts that specify types and amounts of contaminants in the lubricant 91 of the machine 90 from the colors detected by the RGB sensor 53 can also be included in the electronic parts group 50.

In the lubricant deterioration sensor 10, the reflection surfaces 41b and 42b for refracting the optical path 10a are formed on the clearance forming member 40. Therefore, when compared with the configuration in which the optical path 10a from the white LED 52 to the RGB sensor 53 is straightforward, the entirety of the sensor can be miniaturized by placing the white LED 52 and the RGB sensor 53 in close proximity to each other. Further, in the lubricant deterioration sensor 10, the clearance forming member 40 plays the role of bending the optical path 10a as well as the role of forming the oil clearance 40a. Hence, when compared with a configuration separately provided with a member for refracting the optical path 10a instead of the clearance forming member 40, the number of parts can be curtailed.

In particular, in the lubricant deterioration sensor 10, the clearance forming member 40 is made up of the two rectangular prisms 41 and 42 on which there are formed the reflection surfaces 41b and 42b for effecting 90-degree refraction of the optical path 10a. The optical path 10a is subjected to 180-degree refraction by means of the reflection surfaces 41b and 42b of the two rectangular prisms 41 and 42, and the oil clearance 40a is formed between the two rectangular prisms 41 and 42. Hence, the lubricant deterioration sensor can be miniaturized by means of a simple configuration that includes a smaller number of parts.

Further, the lubricant deterioration sensor 10 is equipped with the holder 30 that surrounds at least a portion of the optical path 10a. The surface of the holder 30 is treated with antireflection processing. Hence, the RGB sensor 53 can be prevented from experiencing unwanted reflected light. Consequently, when compared with the configuration in which the RGB sensor 53 experiences unwanted reflected light, the lubricant deterioration sensor 10 can enhance the detection accuracy of colors of contaminants in the lubricant 91.

In the lubricant deterioration sensor 10, the surfaces of the clearance forming member 40 that form the oil clearance 40a; namely, the exit surface 41c of the rectangular prism 41 and the incident surface 42a of the rectangular prism 42, can also be treated with oil repellent treatment. In the lubricant deterioration sensor 10, when the exit surface 41c of the rectangular prism 41 and the incident surface 42a of the rectangular prism 42 are given oil repellent treatment, the exit surface 41c of the rectangular prism 31 and the incident surface 42a of the rectangular prism 42 are less susceptible to stains. Therefore a decrease in detection accuracy of colors of contaminants in the lubricant 91, which would otherwise be caused by stains, can be prevented.

In the lubricant deterioration sensor 10, the layout of the white LED 52 and the RGB sensor 53 may also be different from that described in the embodiment. For instance, in the lubricant deterioration sensor 10, the optical path 10a from the white LED 52 to the RGB sensor 53 may also be straightforward.

In the lubricant deterioration sensor 10, the optical path 10a can also be bended by means of a configuration other than the rectangular prism.

For instance, fluorine coating, a transparent silicone resin, and the like, are available as coating that makes it difficult for stains (sludge) in a lubricant to adhere.

The patent application is based on Japanese Patent Application JP-2010-269097 (filed on Dec. 2, 2010), the subject matter of which is incorporated herein by reference in its entirety.

INDUSTRIAL APPLICABILITY

The lubricant deterioration sensor of the invention enables instant specification of types of contaminants in a lubricant of a machine

REFERENCE SIGNS LIST

10 Lubricant Deterioration Sensor
10a Optical Path
20 Support Member
30 Holder (Optical Path Surrounding Member)
40 Clearance Forming Member
40a Oil Clearance
41 Rectangular Prism
41b Reflection Surface
41c Exit Surface (Surface that makes up Oil Clearance)
42 Rectangular Prism
42a Entrance Surface (Surface that makes up Clearance)
42b Reflection Surface
52 White Led (Light Emitting Element)
53 RGB Sensor (Color Receiving Element)
90 Machine
91 Lubricant

The invention claimed is:
1. An optical sensor, comprising:
a light emitting element for emanating light;
a light receiving element for detecting the light, disposed adjacent to the light emitting element;
a clearance forming member including a first reflection surface, a second reflection surface, and a fluid clearance in which a fluid enters;
a support member supporting the light emitting element, the light receiving element and the clearance forming member;
an optical path surrounding member, wherein the clearance forming member is transmissive so that the light emitted from the light emitting element transmits therethrough, the fluid clearance is provided on an optical path from the light emitting element to the light receiving element such that light reflected from the first reflection surface passes through the fluid clearance before reaching the second reflection surface, and the optical path surrounding member surrounds at least a portion of the optical path.

2. The optical sensor according to claim 1, wherein a space provided on the optical path between the light emitting element and the clearance forming member is formed by a hole, and a space provided on the optical path between the light receiving element and the clearance forming member is formed by a hole.

3. The optical sensor according to claim 1, wherein the light emitting element and the light receiving element are accommodated in the support member at a position opposite to the clearance forming member.

4. The optical sensor according to claim 3, wherein the first reflection surface and the second reflection surface are rectangular prisms having reflection surfaces for bending the optical path, and the fluid clearance is formed between the two rectangular prisms.

5. The optical sensor according to claim 1, wherein a width of a space on the optical path between the light emitting element and the clearance forming member at a side of the clearance forming member is shorter than a width of the space at a side of the light emitting element, and the optical path between the light emitting element and the clearance forming member and the optical path between the light receiving element and the clearance forming member extend in a direction in which the optical sensor is inserted to the mating member.

6. The optical sensor according to claim 4, wherein a groove surrounding an opening of a space on the optical path between the light emitting element and the clearance forming member is formed on a surface of the support member to which the clearance forming member is attached.

7. An optical sensor, comprising:

a light emitting element that emits a light;

a light receiving element that detects the light;

a transmissive part that includes an incident surface to which the light is incident from the light emitting element and an exit surface from which the light incident on the incident surface exits, and defines a gap, into which a lubricant enters, in an optical path from the incident surface to the exit surface; and a first narrowing part that narrows the optical path from the light emitting element to the incident surface.

8. The optical sensor according to claim 7, wherein the first narrowing part includes:

a first part defining a first hole in which the light emitting element is accommodated; and a second part defining a second hole which communicates the first hole with the incident surface and has a first narrowed portion, and an area of the optical path in the first narrowed portion is smaller than an area of the optical path in the first hole.

9. The optical sensor according to claim 7, further comprising a second narrowing part that narrows the optical path from the exit surface to the light receiving element.

10. The optical sensor according to claim 9, wherein the second narrowing part includes:

a third part defining a third hole in which the light receiving element is accommodated; and a fourth part defining a fourth hole which communicates the third hole with the exit surface and has a second narrowed portion, and an area of the optical path in the second narrowed portion.

11. The optical sensor according to claim 7, wherein the transmissive part includes a first rectangular prism and a second rectangular prism, the first rectangular prism has:

a first incident surface which is the incident surface;

a first exit surface orthogonal to the first incident surface;

a first reflection surface which is an inclined surface with respect to an apex angle being right angle and which bends the optical path of the light incident on the first incident surface;

a pair of first side surfaces which sandwich the first incident surface, the first exit surface and the first reflection surface, the second rectangular prism has:

a second incident surface which opposes the first exit surface;

a second exit surface which is orthogonal to the second incident surface and which is the exit surface;

a second reflection surface which is an inclined surface with respect to an apex angle being right angle and which bends the optical path of the light incident on the second incident surface;

a pair of second side surfaces which sandwich the second incident surface, the second exit surface and the second reflection surface, at least one of the first rectangular prism and the second rectangular prism is an object to be fixed, and the optical sensor includes a wall to which a surface including the side surfaces is fixed, in the object to be fixed.

12. The optical sensor according to claim 7, further comprising:

a supporting member which supports the light emitting element, the light receiving element and the transmissive part, and the supporting member includes the first narrowing part.

* * * * *